United States Patent [19]

Rindelaub et al.

[11] Patent Number: 5,521,092

[45] Date of Patent: May 28, 1996

[54] FERMENTATION PLANT

[75] Inventors: Frank A. E. Rindelaub, Bole, Switzerland; Urs Schmutz, Oltingen, Switzerland

[73] Assignee: Frank Alex Erich Rindelaub, Bole, Switzerland

[21] Appl. No.: 200,679

[22] Filed: Feb. 23, 1994

[30] Foreign Application Priority Data

Feb. 25, 1993 [CH] Switzerland ................ 574/93

[51] Int. Cl.[6] .............. B01F 7/04; C12M 1/02; C12M 1/113
[52] U.S. Cl. ............... 435/290.2; 210/151; 422/225; 435/300.1; 435/289.1
[58] Field of Search ...................... 435/285, 286, 435/306, 316; 422/225; 210/150, 151

[56] References Cited

U.S. PATENT DOCUMENTS 3,335,081 8/1967 El-Naggar ................ 435/285

FOREIGN PATENT DOCUMENTS

| 56202 | 7/1982 | European Pat. Off. | ........... 435/287 |
|---|---|---|---|
| 2723341 | 9/1978 | Germany | ........... 210/151 |
| 3239304 | 5/1984 | Germany | ........... 435/316 |
| 122581 | 6/1987 | Japan | ........... 435/286 |

*Primary Examiner*—Jeffrey E. Russel
*Attorney, Agent, or Firm*—Limbach & Limbach

[57] ABSTRACT

The fermentation plant for the biological degradation of organic material and for the collection of the bio gas formed during degradation has a closed container with a filling opening for fresh material and inoculated material and discharge openings for the degradation products as well as a stirring device for mixing the fermentation material. The stirring device has circularly moving stirring blades which are preferably individually driven in the container. Scrapers are provided on the container floor with which heavy precipitates deposited on the container floor are transported in batches to a discharge device. A flow system for a heating medium is also provided on the side walls which is optionally divided into several heating circuits to vary the temperature at various sectors of the heating surface.

6 Claims, 6 Drawing Sheets

5,521,092

FERMENTATION PLANT

FIELD OF THE INVENTION

The invention relates to a fermentation plant for the biological degradation of organic material and for the collection of the bio gas formed during degradation using a closed container with a filling opening for fresh material and circulated or inoculated material and discharge openings for the degradation products and with a stirring device for mixing the fermentation material.

For the purpose of this description, the term fermentation is used in a general sense and comprises aerobic and anaerobic as well as controlled and uncontrolled biotransformation processes, such as fermentation, etc.

In the present description, the term fermentation material is used to designate material present during the fermentation process.

The term fresh material is used to designate the organic material to be degraded, the term inoculate refers to organic material which is removed from the fermentation process and which contains microorganisms and enzymes needed for the fermentation and which is added to the fresh material in the case of discontinuous processes to introduce fermentation.

DESCRIPTION OF THE PRIOR ART

Fermentation plants of the type referred to in the introduction are known, inter alia under the designation bio gas plants. In plants of this type the substances added to a fermenter as fresh material with partially admixed inoculate are heated to the process temperature previously or in the fermenter and mixed by a stirring system during the process. The resultant gases may, for example, be delivered to an energy supply plant or also used to cover the plant's own process energy.

Known bio-gas plants have the disadvantage that the circulating stirring mechanisms are very laborious to produce technically, i.e. above all mechanically, and consume a great deal of energy and still do not ensure homogenous mixing and a temperature distribution in the fermentation material that are optimum for the process.

OBJECTS OF THE INVENTION

It is an object of the present invention to overcome these disadvantages by providing a fermentation plant that is mechanically simpler and hence cheaper to produce and operate which also ensures optimum mixing and heat distribution.

BRIEF SUMMARY OF THE INVENTION

This object is solved according to the invention in that the stirring device has circularly moving stirring blades. The stirring blades may either be associated with a drive mechanism moving them simultaneously in the container or be individually driven, i.e. independent from one another.

BRIEF DESCRIPTION OF THE INVENTION

The stirring blades consist advantageously of paddles secured with holders and cross-bars to shafts which are disposed substantially transverse to the vertical central plane of the container.

According to a preferred embodiment of the invention a flow system for a heating medium is provided on the side walls which may be subdivided into several heating circuits to vary the temperature at various sectors of the heating surface. The flow system is preferably disposed on the outside of the container walls.

According to another preferred embodiment of the invention, scrapers are provided on the container floor with which heavy precipitates deposited on the container floor are transported in batches to a discharge device. These scrapers may either be coupled with the drive for the stirring blades or may also have separate drives so that the conveying capacity can be flexibly adapted.

BRIEF DESCRIPTION OF THE DRAWINGS

Preferred embodiments of the invention are described hereinbelow with reference to the appended drawings. There are shown in FIG. 1 a side view of a fermentation device with the side wall of the container cut away FIG. 2 a top plan view of a fermentation device with the container ceiling cut away FIG. 3 a front view of a fermentation device with the front wall of the container cut away FIGS. 4A and 4B a front view and side view respectively similar to the views of FIGS. 3 and 1 showing details of the stirring device FIG. 5 a further detail of the stirring device FIG. 6 an arrangement of several devices connected together for pre-composting, fermentation and post-composting.

DETAILED DESCRIPTION OF THE INVENTION

Figure 1:
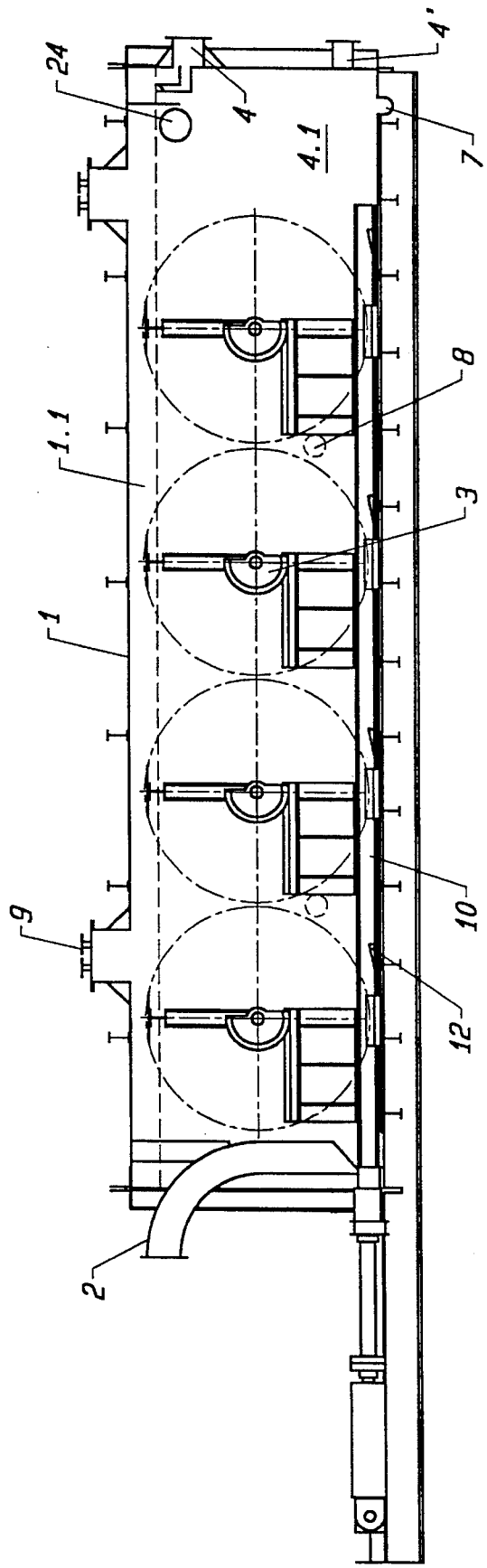
Figure 2:
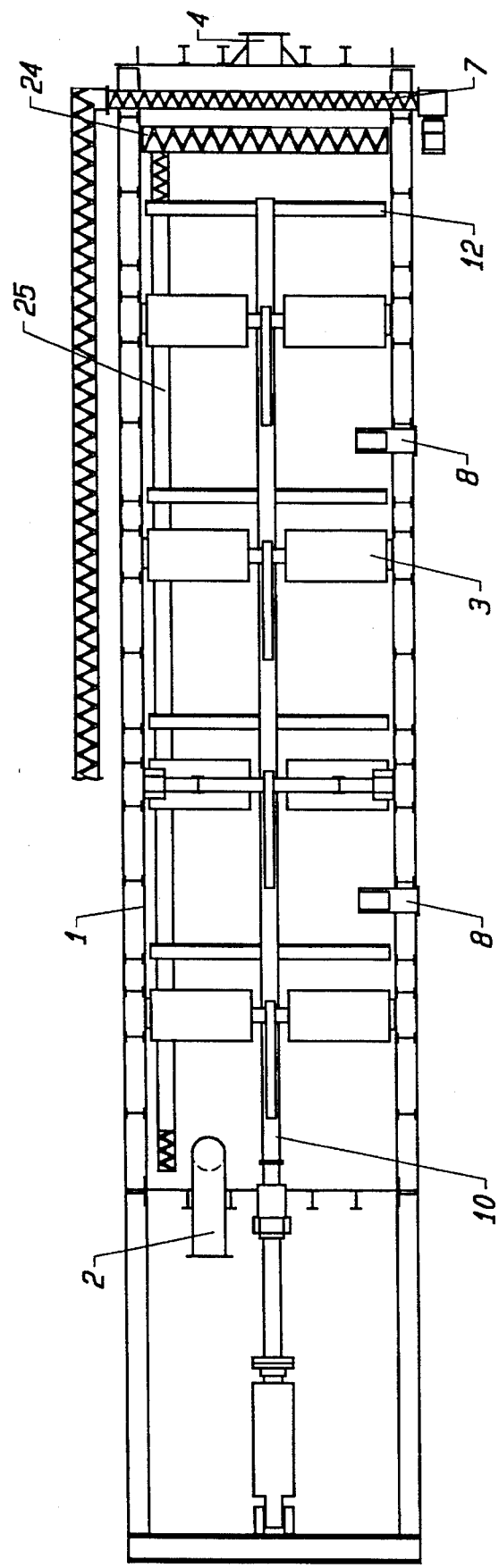
Figure 6:
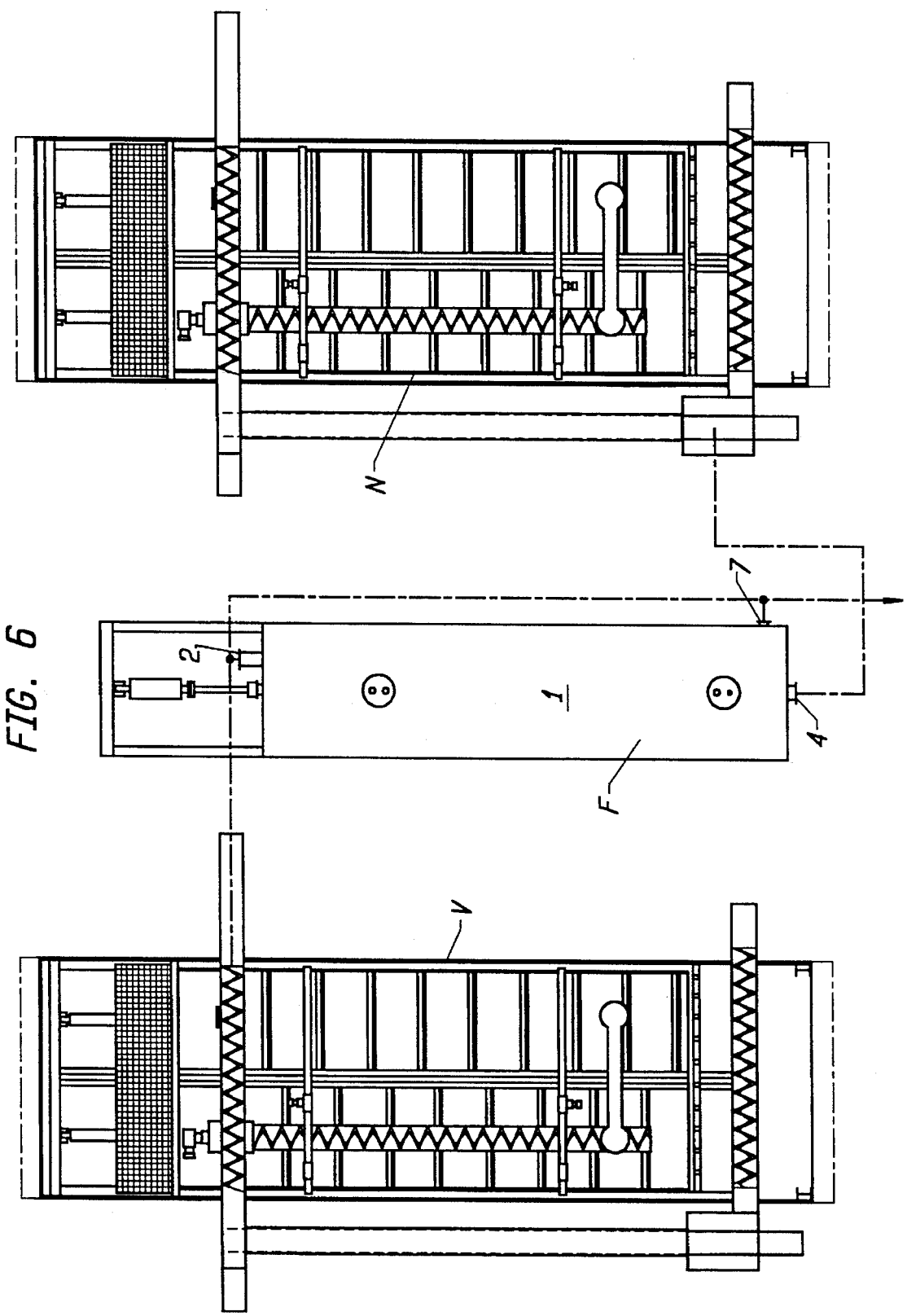

The fermentation device shown in FIGS. 1 and 2 consists of a rectangular closed container 1 with an inner chamber 1.1 (see also FIG. 4B) having flat walls for the uptake of the fermentation material 4.1. The container has a filling opening 2 for fresh material and circulated or inoculated material and discharge openings 4 and 7 (see also FIG. 3) for the degradation products. As shown in FIG. 6, material is preferably delivered to container 1 through discharge opening 2 from a pre-composting plant V, and delivered from discharge openings 4, 7 to a post-composting plant N. The container also has sample removal openings 8 (see also FIG. 3) disposed in the side walls and gas removal openings 9 disposed in its ceiling.

Located in the container is a stirring device 3 for mixing the fermentation material and a floor scraping device 12 for discharging deposited heavy precipitates such as sand, stones, metal parts, etc. These two functions are carried out by various parts of the stirring device 3.

Figure 3:
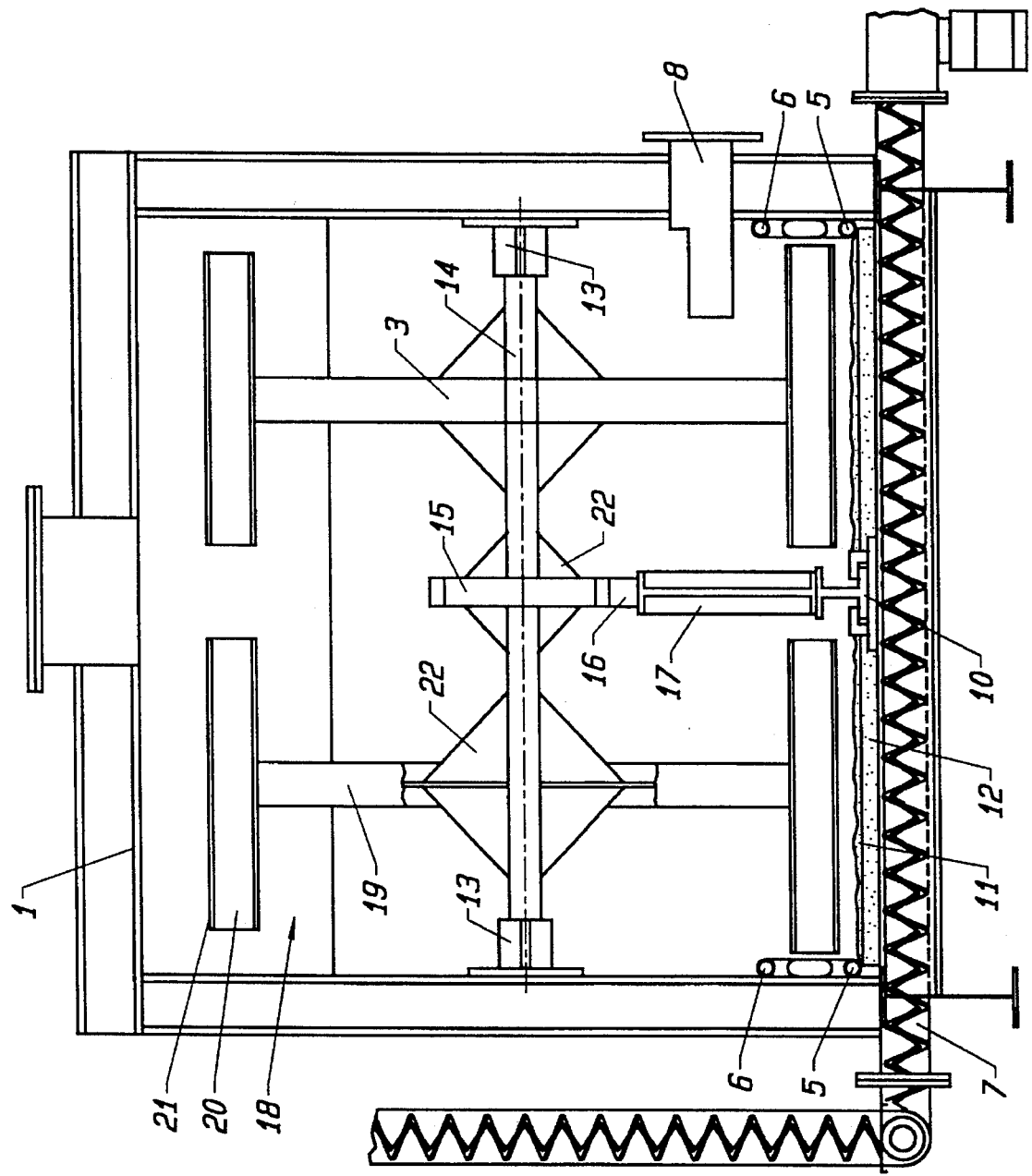
Figures 4A, 4B:
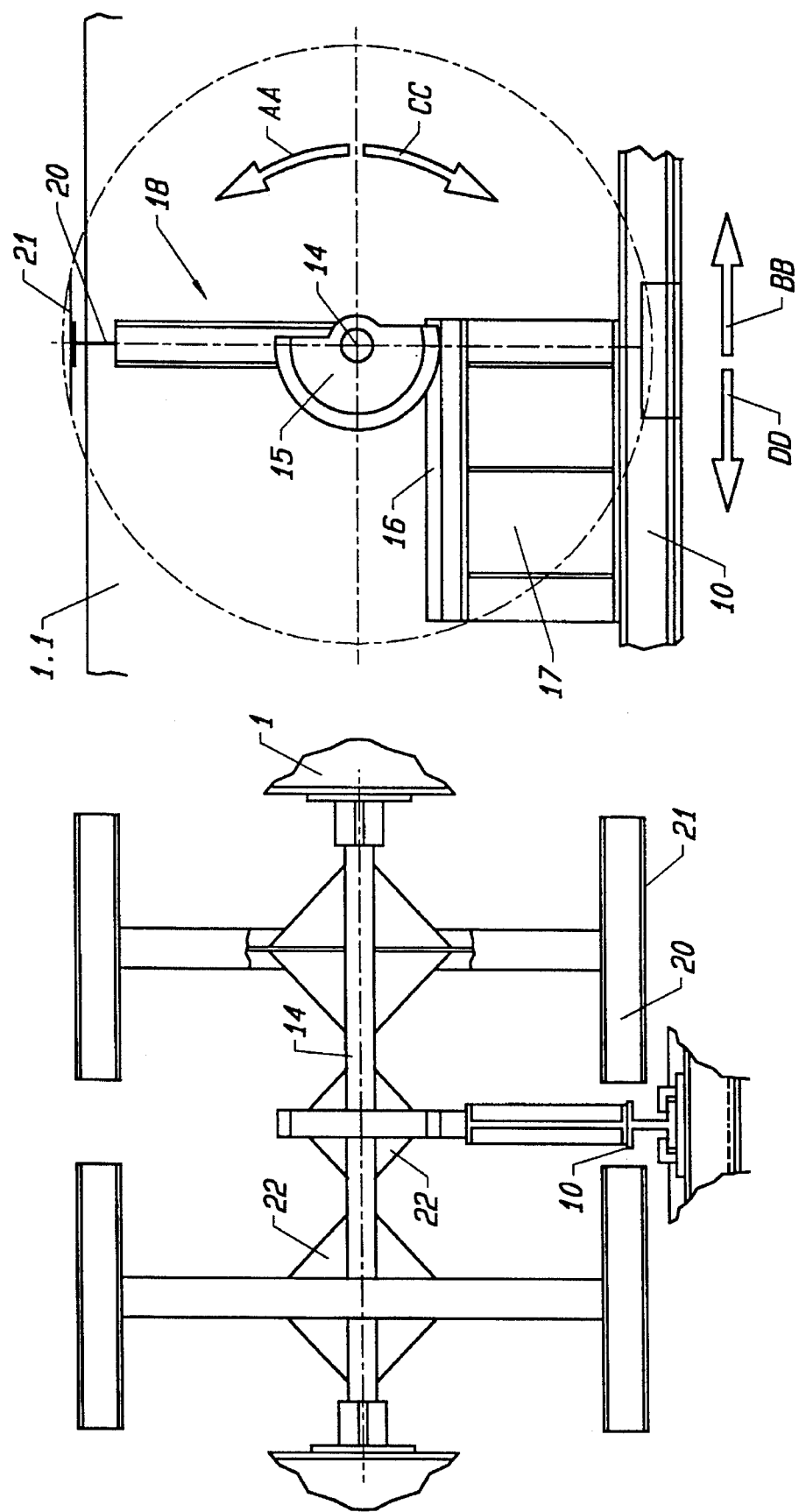

The mixing is effected by a system of stirring blades which are shown in detail in FIGS. 3, 4A and 4B.

As most clearly shown in FIG. 3, bearings 13 are arranged in pairs about half way up the inner sides of the side walls of the container 1 (see also FIG. 4A). One shaft 14 is carried in one pair of bearings 13. In all, four shafts 14 disposed in this manner between the side walls are evenly distributed over the length of the container 1.

Disposed on the shafts in the middle thereof is a driving toothed wheel 15 which in the present case comprises a sector of about 180 degrees. The toothed wheel meshes into a correspondingly toothed, linearly driven rack rail 16. The rack rail 16 is associated with a connecting rod 10 (also shown in FIGS. 1, 2, 4A and 4B) via a support 17 which extends over the entire length of the container 1 and which is moved backwards and forwards by a drive device disposed outside the container. It goes without saying that other types of drives, e.g. individual hydraulic drives for each shaft, etc. may be used as alternatives.

Stirring blades 18 are disposed in each case in the middle between driving toothed wheel and the bearings. These consist of a bar 19 vertical to the shaft 14 secured thereto, at both ends of which are in each case one cross-bar 20 and a paddle 21 secured thereto, parallel to the shaft. Bars 19 and cross-bar 20 consist in the present embodiment of H-profiles, the paddles 21 consist of sheet metal. The connection between shaft and bars, and between shaft and toothed wheel sector, is preferably reinforced with sheet metal angles 22 (see also FIG. 4A).

The mixing function is most clearly visible in FIG. 4B. The driving toothed wheel sector 15 and hence the shaft 14 and the stirring blades 18 are rotated counter-clockwise according to the arrow AA by linear displacement to the right of the connecting rod 10 and hence the support 17 and the rack rail 16 according to the arrow BB. This rotation draws the upper paddle downwards through the fermentation material and thus conveys material located in the upper layers downwards. At the same time the paddle initially located at the bottom and thereby material is pulled upwards thereby from underneath. This circulation effects an excellent mixing of the fermentation material. The process is repeated at intervals as required, thus for example whenever the gas development accompanying the fermentation process abates or ceases. As illustrated in FIG. 4B, the driving toothed wheel sector 15, shaft 14 and stirring blades 18 may also be rotated clockwise (arrow CC) with the support 17 and rack rail 16 moving according to the arrow DD.

Figure 5:
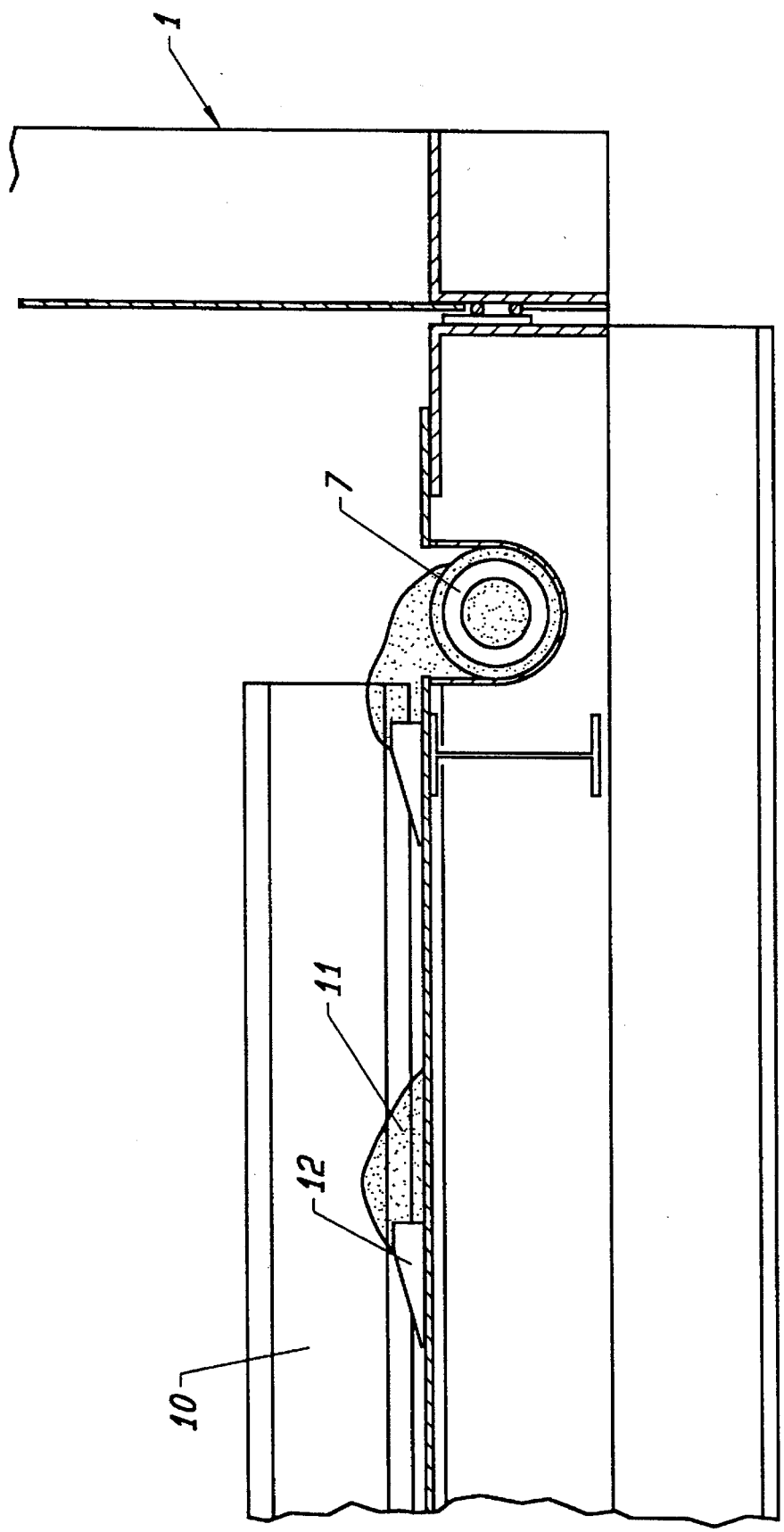

The discharge of deposited heavy precipitates 11 is effected by scrapers 12 which are most clearly visible in FIG. 5 (but also shown in FIG. 3). The scrapers 12 are associated with the connecting rod 10 and slide on the floor of the container 1. They have a wedge-shaped cross section with ramp-shaped rear and steep front. During the backwards movement (to the left in FIG. 5), the deposited heavy substances reach the front side of the scraper via the ramp surface. During the next forwards movement conveyance in the direction of the discharge worm 7 is then achieved with the steep front side.

Alternatively, the scrapers 12 may be shaped like flaps which lift with the linear backwards movement of the stirring device (to the left in FIG. 5) thereby sliding over the deposited material whereas they sink during the forwards shifting of the stirring device (to the right in FIG. 5) and push the deposits 11 in the vicinity of the discharge worm 7.

The scrapers 12 may preferably be actuated independent of the drive of the stirrer blades.

As most clearly visible in FIG. 3, a flow system for a heating medium with an inlet conduit 5 and a return conduit 6 is disposed along the side walls in the lower area. Heat transfer occurs directly to the fermentation material from the heat flow system. Dynamic heat transfer results from the circular movement of the stirring device. This heats the fermentation material to the desired process temperature and compensates radiation losses via the container jacket.

The flow system for the heating medium may be divided into several heating circuits which may be provided with different heating capacities to vary the temperature at various sectors of the heating surface. This ensures greater flexibility in controlling the course of temperature permitting optimum adaptation to the requirements of the process.

As an alternative to heating disposed inside the container, the heating medium conduits may be disposed on the outside of the container walls. This has the advantage that the inner walls are smooth and the collection of sediment is reduced.

Since the freshly filled in fermentation material has to be heated up at the beginning of the process and since heating should only be effected with small temperature differences to protect the bacteria, a particularly large heating surface is useful in the area of the first stirring blade which also includes the end wall. Since during the further course of fermentation only the heat loss has to be compensated, the heat applied from outside may be reduced step by step, with the result that the outer heating elements may become progressively smaller.

The heating elements are preferably made in the form of twin-wall flow systems.

The fermentation material is mixed by the movement of the stirrer blades 18 (best shown in FIG. 4B) and divided up by the shearing forces generated. The fact that the stirring device largely extends above the entire inner chamber 1.1 (FIG. 1) filled with fermentation material ensures optimum mixing of the entire fermentation material, which leads to high process stability and effective degassing of the fermentation material together with the mentioned, improved heating.

A rectangular or multi-angled cross section of the container with flat walls is optimal for the efficacy of the stirring device 3.

The fermentation material is in a relatively undisturbed state in the space between the last stirring blades and the discharge openings 4,4' (FIG. 1) with the result that a very compact swimming cake could form on the surface which could no longer be discharged without difficulty through the opening 4 (FIG. 1). To prevent this, a substantially horizontal conveying spiral 24 (FIGS. 1 and 2) is disposed in this area substantially transverse to the longitudinal axis of the plant. This conveying spiral has two mutually opposingly threaded halves in such a manner that material is conveyed from the two lateral areas to the middle with uniform direction of rotation.

Another transport means, specifically a closed conveying spiral 25 (FIG. 2), extends in longitudinal direction through the plant and serves to convey material from the end area back to the initial area of the plant. This back-mixing of already fermented material to the fresh material serves to control physical and biotechnological process parameters. This back-mixing spiral may either be disposed in the floor or in the area of the surface of the fermentation material, laterally or in the middle.

FIG. 6 shows the advantageous arrangement of the present fermentation device F together with an associated upstream composting device V and a downstream composting device N. Depending on the size of the composting device, it may be appropriate to employ several fermentation devices according to the present invention in series. Suitable composting devices are, for example, the object of Swiss patent application No. 03106/92-8, Canadian patent application No. 2107646; European patent application No. 93810694.5 and U.S. patent application Ser. No. 08/131899, now U.S. Pat. No. 5,434,080.

We claim:

1. A fermentation plant for the biological degradation of organic material into degradation products and for the collection of the bio gas formed during degradation, comprising:
- a closed container having a filling opening for fresh organic material and circulated or inoculated material and discharge openings for the degradation products; and
- a stirring device for mixing fermentation material within the container, wherein the stirring device has independently driven and circularly moving stirring blades.

2. A fermentation plant according to claim 1, wherein the stirring blades consist of bars, cross-bars and paddles, which are secured to shafts which are disposed substantially transverse to the vertical central plane of the container.

3. A fermentation plant according to claim 1, wherein the container includes side walls and wherein a flow system for a heating medium is provided on the side walls.

4. A fermentation plant according to claim 3, wherein a flow system for the heating medium is divided into several heating circuits to vary the temperature at various sectors of the flow system.

5. A fermentation plant according to claim 1, wherein there are scrapers on the floor of the container with which heavy precipitates deposited on the container floor are transported in batches to a discharge device.

6. A fermentation plant according to claim 1, wherein the filling opening is located at a filling area of the container and at least one of the discharge openings is located at an end area of the container and wherein transport means are disposed in the container for transporting fermentation material in a substantially longitudinal direction from the end area to the filling area.

* * * * *